United States Patent [19]

Zinnes et al.

[11] 4,148,922
[45] Apr. 10, 1979

[54] 3-[2-(DIALKYLAMINO)ETHYL]-2-(BENZYL)-INDOLES

[75] Inventors: Harold Zinnes, Rockaway; Martin L. Schwartz, Parsippany, both of N.J.

[73] Assignee: Warner-Lambert Company, Morris Plains, N.J.

[21] Appl. No.: 902,582

[22] Filed: May 4, 1978

[51] Int. Cl.² .................. C07D 209/16; C07D 209/18; A61K 31/40

[52] U.S. Cl. .............................. 260/326.12 R; 546/85; 424/274

[58] Field of Search ............................... 260/326.12 R

[56] References Cited

U.S. PATENT DOCUMENTS 3,931,229 1/1976 Zinnes ......................... 260/326.12 R
3,931,230 1/1976 Zinnes et al. ................ 260/326.12 R Primary Examiner—Mark L. Berch
Attorney, Agent, or Firm—David B. Ehrlinger; Stephen Raines; Frank S. Chow

[57] ABSTRACT

3-[2-(Dialkylamino)ethyl]-2-(benzyl)indoles having in free base form the formula

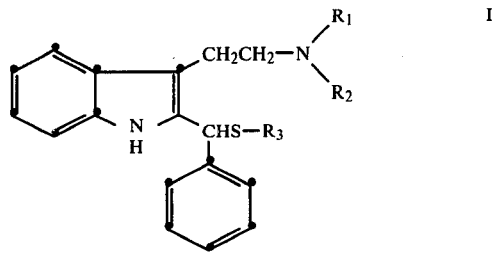

where $R_1$ and $R_2$ are lower alkyl groups and $R_3$ is a phenyl, carboalkoxymethyl, lower alkyl or hydroxyethyl group. The compounds of the invention exhibit anti-aggression and anti-secretory properties and are indicated in the management of aggression and gastric hypersecretion.

5 Claims, No Drawings

3-[2-(DIALKYLAMINO)ETHYL]-2-(BENZYL)INDOLES

SUMMARY AND DETAILED DESCRIPTION

The present invention relates to 3-[2-(dialkylamino)-ethyl]-2-(benzyl)indoles having in free base form the formula

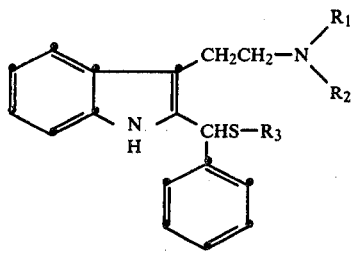

where $R_1$ and $R_2$ are lower alkyl groups and $R_3$ is a phenyl, carboalkoxymethyl, lower alkyl or hydroxyethyl group. For purposes of the invention the term "lower alkyl" signifies a straight or branched chain alkyl group of 1 to 4 carbon atoms such as methyl, ethyl, n-propyl, isopropyl and n-butyl.

The compounds of the invention form salts with pharmaceutically acceptable acids and these salts are included within the scope of the invention. These salts include, for example, salts formed with acids such as hydrochloric, hydrobromic, sulfuric, nitric and acetic acid and the like.

The above compounds and their salts are characterized by anti-aggression activity. For example, when administered intraperitoneally to isolated fighting mice the compound of formula I where $R_1$ and $R_2$ are methyl groups and $R_3$ is ethyl serves to reduce aggression when tested by a standard protocol (see Yen et al., Arch. Intl. Pharmacodynamics, 123, pages 179-185, 1959). The compound also exhibits anti-secretory activity. For example, when administered intraperitoneally to the Shay rat with ligated pylorus in replicate at a dose of 20 mg./kg., gastric secretion and gastric acidity are reduced, on the average, by 48% and 44%, respectively (Shay et al., Gastroenterology 5, 43, 1945; Grossman et al., ibid. 38, 343, 1960).

These compounds are useful therefore as anti-aggression agents and anti-secretory agents.

The compounds of the present invention can be administered orally and by such compositions as tablets, pills, dispersible powders and the like. The active ingredient is mixed with at least one inert pharmaceutical diluent such as lactose and suitable granules, using agents such as water or alcohol, and the resulting granules compressed into tablets utilizing standard tableting procedures.

Liquid pharmaceutically administerable compositions are prepared by dissolving or suspending the active ingredient in a pharmaceutically acceptable carrier such as water or syrup.

The compounds of this invention can be administered in dosages varying between 10-25 mg. per kg. of body weight 2 to 3 times daily. The precise dosage regimen can be varied depending on the mode of adminstration and the condition being treated, using procedures which are conventional in the healing arts.

The compounds are produced, according to the invention by reacting a quaternary salt of formula

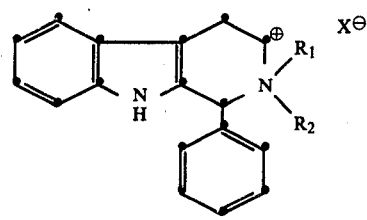

where $R_1$ and $R_2$ have the above-described meaning, with the salt of a thiol of formula $MSR_3$ where $R_3$ has the above-described meaning and M is an alkali metal cation or an alkaline earth metal cation such as sodium, potassium, or calcium.

The thiol salt is conveniently generated in situ by treating the thiol with aqueous alkali or with a base such as sodium hydride in a non-aqueous solvent such as tetrahydrofuran. The main reaction is generally carried out in the same basic solvent system used to generate the thiol salt although a co-solvent such as hexamethylphosphorous triamide (HPMA), dimethylsulfoxide (DMSO), or diethylformamide (DMF) may be added. The reaction temperature may be varied from room temperature to the reflux temperature of water.

The thiol starting materials are commercially available. The quaternary salt starting materials are prepared as described by T. Hoshino and Y. Kotake, Ann. 516, 76 (1935); C.A. 29, 2957 (1935), which description is incorporated herewith by reference.

The invention is illustrated by the following examples.

EXAMPLE 1

A mixture of 28.0 g. (0.07 mol.) of 3,4-dihydro-2,2-dimethyl-1-phenyl-1H,9H-pyrido[3,4-b]indolium iodide, 7.7 g. (0.07 mol.) of thiophenol, 70 ml. of 1.0 N sodium hydroxide, and 200 ml. of water was refluxed with stirring for 3 hours and allowed to cool to 25° C. The crystalline product which separated, 3-[2-(dimethylamino)ethyl]-2-[α-(phenylthio)benzyl]-indole, was collected and recrystallized from 150 ml. of isopropyl alcohol; m.p., 139°-141° C.

The corresponding hydrochloride salt is obtained by dissolving the free base in ether, treating the solution with dry hydrogen chloride until precipitation of the product is complete, and isolating the product. The hydrobromide and sulfate are obtained by treating the free base in ether solution with dry hydrogen bromide or with sulfuric acid.

EXAMPLE 2

The reaction was carried out as in the previous example using 4.5 g. (0.07 mol.) of ethanethiol in place of thiophenol. The material which precipitated from the reaction mixture was dissolved in 1000 ml. of ether. The solution was washed successively with 1N sodium hydroxide, water, and saturated sodium chloride solution. The residual product, 3-[2-(dimethylamino)ethyl]-2-[α-(ethylthio)benzyl]-indole, obtained after drying and evaporation of the dried solution was recrystallized from 150 ml. of isopropyl ether; m.p., 120°-123° C.

EXAMPLE 3

A mixture of 2-mercaptoethanol (6.48, 0.08 mol., 98%) and 3,4-dihydro-2,2-dimethyl-1-phenyl-1H, 9H-pyrido[3,4-b]-indolium iodide (28.3 g., 0.07 mol.) in 1 N NaOH solution (70 ml., 0.07 mol.) and water (180 ml.) was refluxed for 17 hours and allowed to cool to 25° C. The aqueous phase was decanted, and the residue was dissolved in ethyl acetate (400 ml.). The organic layer was washed successively with 1 N NaOH solution, 2 portions of water, saturated NaCl solution, and was dried over sodium sulfate and evaporated to dryness. The residual product, 2-[({3[2-(dimethylamino)ethyl]-1H-indol-2-yl}phenylmethyl)-thio]ethanol, was recrystallized from acetonitrile (100 ml.); m.p. 138°-140° C.

EXAMPLE 4

To a slurry of sodium hydride (1.27 g., 0.03 mol., 57% mineral oil dispersion), in tetrahydrofuran (THF) (50 ml.), at 25° C., was slowly added a solution of methyl mercapto acetate (3.25 g., 0.03 mol., 98%) in tetrahydrofuran (THF) (25 ml.). Solid 3,4-dihydro-2,2-dimethyl-1-phenyl-1H,9H-pyrido [3,4-b]indolium iodide (12.12 g., 0.03 mol.) and HMPA (50 ml.) were added after hydrogen evolution ceased and the mixture was stirred at 25° C., for 22 hours. The reaction mixture was poured into water (1,000 ml.) and the oily mixture was extracted with ethyl acetate (600 ml.). The organic layer was washed with 1 N NaOH solution, 2 portions of water, saturated NaCl solution, and dried over NaSO4, and evaporated. The residual product, methyl [({3-[2-dimethylamino)ethyl]-1H-indol-2-yl}-phenylmethyl)-thio]acetate, was recrystallized from cyclohexane (140 ml.); m.p. 94°-96° C.

By the procedure of the foregoing examples, when the indolium iodide is replaced by the corresponding 2,2-di-(n-propyl)iodide quaternary salt, the products are:

3-{2-[Dipropylamino]ethyl}-2-[α-(phenylthio)benzyl]indole
3-{2-[Dipropylamino]ethyl}-2-[α-(ethylthio)benzyl]indole
2-[({3-[2-(Dipropylamino)ethyl]-1H-indol-2-yl}-phenylmethyl)thio]ethanol
methyl[({3-[2-(dipropylamino)ethyl]-1H-indol-2-yl}-phenylmethyl)thio]acetate

We claim:
1. A compound of the formula

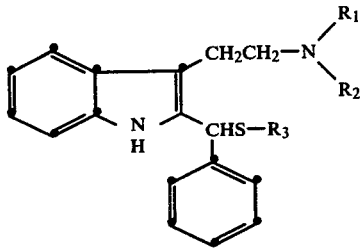

I where $R_1$ and $R_2$ are alkyl groups having 1 to 4 carbon atoms and $R_3$ is phenyl, carboloweralkoxymethyl, lower alkyl or hydroxyethyl and the corresponding pharmaceutically acceptable acid addition salts.

2. A compound according to claim 1 which is 3-[2-(dimethylamino)ethyl]-2-[α-(phenylthio)benzyl]indole.
3. A compound according to claim 1 which is 3-[2-(dimethylamino)ethyl]-2-[α-(ethylthio)benzyl]indole.
4. A compound according to claim 1 which is 2-[({3[2-(dimethylamino)ethyl]-1H-indol-2-yl}phenylmethyl)thio]ethanol.
5. A compound according to claim 1 which is methyl[({3-[2-(dimethylamino)ethyl]-1H-indol-2-yl}phenylmethyl)-thio]acetate.

* * * * *